(12) United States Patent
Solomon et al.

(10) Patent No.: US 12,144,946 B1
(45) Date of Patent: Nov. 19, 2024

(54) APPARATUS FOR FORMING BALLOON LAYER AND RELATED METHODS

(71) Applicant: Bard Peripheral Vascular, Inc., Tempe, AZ (US)

(72) Inventors: Clint Solomon, Gilbert, AZ (US); Adriana Alvarado-Salazar, Gilbert, AZ (US); Melissa Boyle, Phoenix, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 571 days.

(21) Appl. No.: 17/197,577

(22) Filed: Mar. 10, 2021

Related U.S. Application Data

(60) Provisional application No. 62/987,664, filed on Mar. 10, 2020.

(51) Int. Cl.
  *A61M 25/10* (2013.01)
  *A61C 8/00* (2006.01)
  *B05D 3/10* (2006.01)

(52) U.S. Cl.
  CPC . *A61M 25/1029* (2013.01); *A61M 2025/1075* (2013.01); *A61M 2207/00* (2013.01)

(58) Field of Classification Search
  CPC .... A61M 2207/10; B29C 55/00; B29C 55/26; B29C 61/08
  See application file for complete search history.

(56) References Cited

U.S. PATENT DOCUMENTS

| | | | |
|---|---|---|---|
| 2,168,993 A | 8/1939 | Joseph | |
| 5,718,861 A | 2/1998 | Andrews et al. | |
| 5,807,520 A | 9/1998 | Wang et al. | |
| 6,500,146 B1 | 12/2002 | Pinchuk et al. | |
| 6,572,813 B1 * | 6/2003 | Zhang | B29C 55/24 264/903 |
| 6,946,092 B1 * | 9/2005 | Bertolino | A61M 25/1029 264/573 |
| 8,236,223 B2 | 8/2012 | Graves et al. | |
| 8,610,899 B2 | 12/2013 | Hadcock et al. | |
| 8,715,229 B2 * | 5/2014 | Davies, Jr. | A61M 25/104 604/103.08 |
| 9,533,126 B1 * | 1/2017 | Tayebi | A61M 25/1029 |
| 9,913,958 B2 * | 3/2018 | Ciurea | B29C 57/04 |
| 10,022,906 B2 | 7/2018 | Gada et al. | |
| 2016/0031150 A1 * | 2/2016 | Gada | A61L 31/06 264/564 |

FOREIGN PATENT DOCUMENTS

CN 105599284 A 5/2016

\* cited by examiner

*Primary Examiner* — Cachet I Proctor
(74) *Attorney, Agent, or Firm* — Dickinson Wright PLLC; Andrew D. Dorisio

(57) ABSTRACT

An apparatus is for forming a balloon layer, such as on an expanded base balloon. The apparatus includes a mandrel supporting the expanded base balloon. At least one gripper is provided for gripping the balloon layer, and an actuator is for stretching the balloon layer over the expanded base balloon, such as by moving the at least one gripper. Related methods for forming a balloon layer are also disclosed.

22 Claims, 15 Drawing Sheets

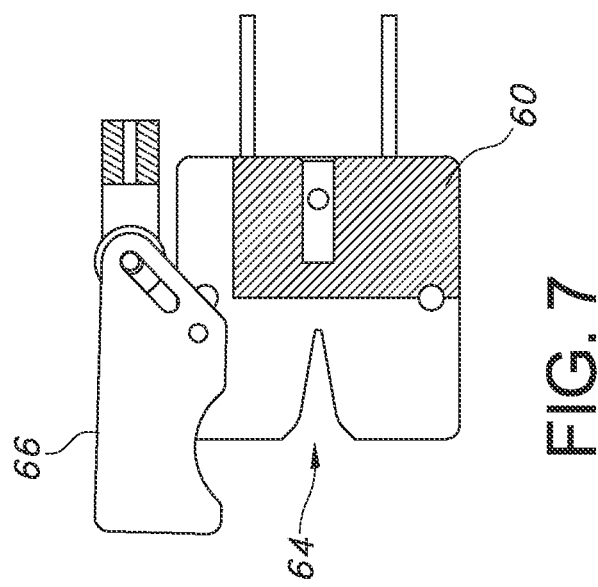
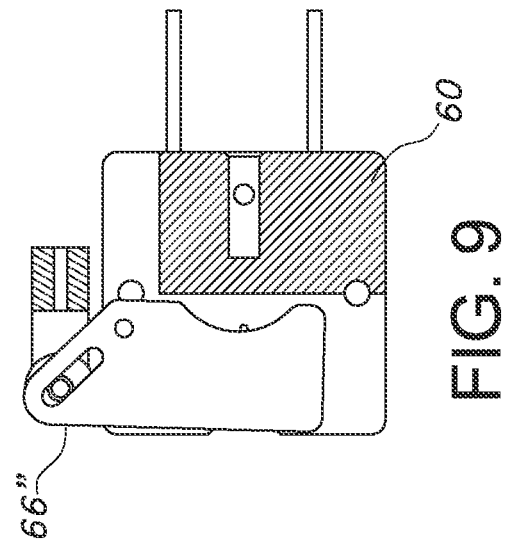
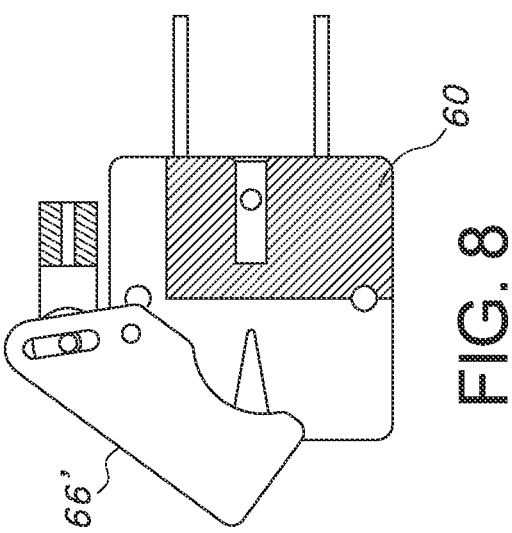

APPARATUS FOR FORMING BALLOON LAYER AND RELATED METHODS

BACKGROUND OF THE INVENTION

Inflatable balloon catheters are often used to treat vessels in the human body. The inflatable balloons are typically of the non-compliant variety, meaning the balloon once inflated to a nominal diameter does not result in a meaningful increase upon further pressurization. As can be appreciated, this property of non-compliance may be desirable for interventions involving the compaction of calcified lesions, especially in narrow vessels.

Constructing such a balloon usually involves the use of one or more layers of fibers in a wall of the balloon. This may be achieved by winding the fibers along or around a base balloon forming a mandrel. Completion of such a fiber-based balloon often necessitates the application of an outer coating (or "outer"), such as a film layer, which covers the underlying (fiber) layer. In addition to enhancing the resulting properties of the balloon, this outer layer ensures that the balloon presents a smooth and consistent working surface.

Applying such a film to the balloon may be done manually, such as by simply placing the film over a mandrel including a partially completed base balloon. However, this manual application may lead to inconsistent results due to operator variability, as well as the varying material properties of different types of films. This is especially true when the balloon layer is to be formed by longitudinally stretching a tubular film over the base balloon, which cannot be done manually with consistent results.

Accordingly, a need is identified for an apparatus for forming a balloon layer, such as an outer layer formed of a film, is provided. The apparatus would at least partially automate the process, thereby reducing the need for operator intervention and potentially providing more consistent and reliable results.

SUMMARY OF THE INVENTION

An object of the disclosure is to provide an apparatus for forming a balloon layer, such as an outer layer of film, on a base balloon in a reliable, efficient, and highly repeatable manner.

According to one aspect of the disclosure, such an apparatus for forming a balloon layer on an expanded (e.g., inflated) base balloon is provided. The apparatus includes a mandrel supporting the base balloon. At least one gripper is provided for gripping the balloon layer. An actuator is also provided for stretching the balloon layer over the base balloon.

In one embodiment, at least one holder is provided for holding a first portion of the balloon layer. The actuator is configured to move the at least one gripper in a first direction to stretch the balloon layer over the base balloon while the holder is holding the first portion of the balloon layer in place. Another actuator may also be provided for moving the at least one holder in a second direction opposite the first direction.

The at least one gripper may comprise a first gripper for gripping a first portion of the balloon layer adjacent a first end of the mandrel. A second gripper may also be provided for gripping a second portion of the balloon layer adjacent a second end of the mandrel. A first holder may also be provided for holding a third portion of the balloon layer stationary while the first gripper is stretching the balloon layer by gripping and moving the first portion of the balloon layer. A second holder may also be provided for holding a fourth portion of the balloon layer stationary while the second gripper is stretching the balloon layer by gripping and moving the second portion of the balloon layer.

The apparatus may include a heater for heating the balloon layer. A carriage may be provided for moving the heater along the base balloon. The apparatus may further include a rotary actuator for rotating the mandrel relative to the heater.

The heater may comprise a nozzle for supplying heated air, or a heated die for contacting the balloon layer. The heated die may include a tapered notch configured for receiving and heating a portion of the balloon layer adjacent a transition from a cone of the base balloon to a neck of the base balloon. An actuator may be provided for locating the heated die relative to the transition, and a pusher for urging the balloon layer at the transition into contact with the heated die.

The apparatus may also include a mandrel rest. The mandrel rest may be configured to magnetically couple with the mandrel outboard of the at least one gripper along the same axis. The mandrel rest may include a V-shaped face to avoid interfering with the balloon layer supported by the mandrel.

According to another aspect of the disclosure, an apparatus for forming a balloon layer is provided, which includes an expanded base balloon supported by a mandrel. A first gripper is provided for gripping a first portion of the balloon layer adjacent a first end portion of the base balloon. A second gripper is also provided for gripping a second portion of the balloon layer adjacent a second end portion of the base balloon.

In one embodiment, at least one holder is provided for holding a third portion of the balloon layer. A first actuator may be configured to move the first gripper in a first direction to stretch the balloon layer over the base balloon, and a second actuator configured to move the second gripper in a second direction to stretch the balloon layer over the base balloon. The apparatus may further include a heated die for contacting an outer surface of the balloon layer.

Still a further aspect of the disclosure pertains to a method for forming a balloon layer on an expanded base balloon. The method comprises forming the balloon layer on the expanded base balloon by stretching the balloon layer over the base balloon.

The method may further include the step of applying heat to the balloon layer after the forming step. The step of rotating the base balloon may also occur during the applying step. The step of applying heat may comprise contacting the balloon layer with a heated die.

BRIEF DESCRIPTION OF THE DRAWINGS

The above and further advantages of the present disclosure may be better understood by referring to the following description in conjunction with the accompanying drawings in which:

FIGS. 7, 8, and 9 are side views showing various operational states of the heated die and pusher;

Figure 1:
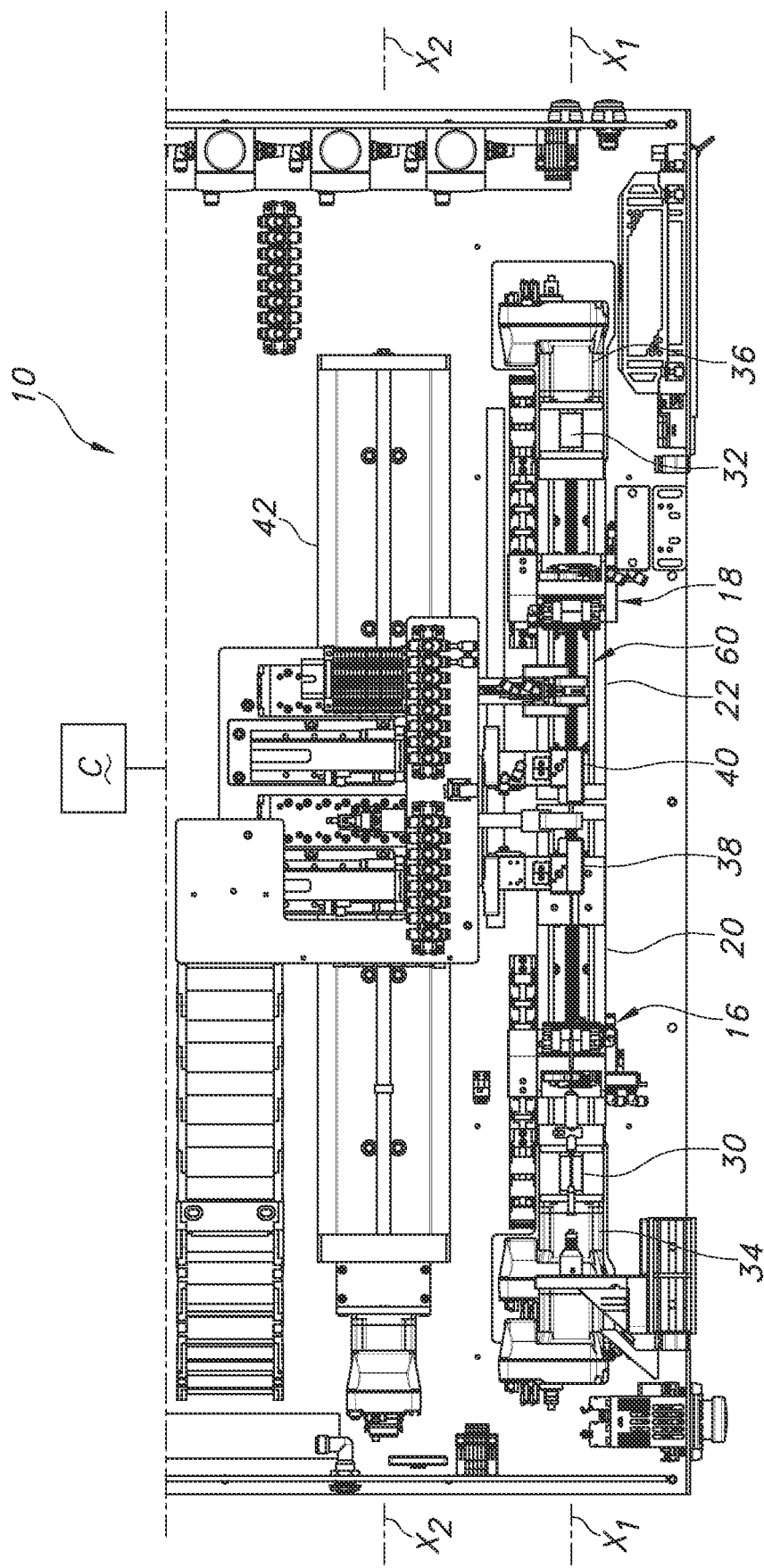
FIG. 1 is plan view of the apparatus.

The dimensions of some of the elements may be exaggerated relative to other elements for clarity or several physical components may be included in one functional block or element. Further, sometimes reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth to provide a thorough understanding of the presently disclosed invention(s). The disclosed embodiments may be practiced without these specific details. In other instances, well-known methods, procedures, components, or structures may not have been described in detail so as not to obscure the present inventive concepts.

The invention is not limited in its application to the details of construction and the arrangement of the components set forth in the following description or illustrated in the drawings. The inventive concepts disclosed are capable of other embodiments or of being practiced or carried out in various ways. Also, it is to be understood that the phraseology and terminology employed herein are for the purpose of description and should not be regarded as limiting.

Certain features of the disclosed embodiments that are, for clarity, described in the context of separate embodiments, may also be provided in combination in a single embodiment. Conversely, various features of the invention that are, for brevity, described in the context of a single embodiment, may also be provided separately or in any suitable sub-combination.

With reference to FIGS. 1-11, an apparatus 10 for forming a balloon layer, such as an outer layer on a base balloon designed for performing percutaneous transluminal angioplasty or like procedures, is described. As will be outlined further in the description that follows, the apparatus 10 is configured to automatically apply the balloon layer to a pre-formed base balloon 12. The base balloon 12 may comprise one or more layers of material, including possibly fibers in various configurations or patterns.

The base balloon 12 may be expanded, such as by being partially or fully inflated with fluid under pressure and provided on a mandrel 14. Consequently, the base balloon 12 may have the typical shape of such a balloon, with a cylindrical center or barrel portion, tapering cone portions, and necked portions for connecting to a catheter. However, this disclosure is not limited to any size, shape, or type of base balloon to which a material layer is to be applied using the disclosed apparatus 10 and techniques, in whole or in part.

Figure 12:
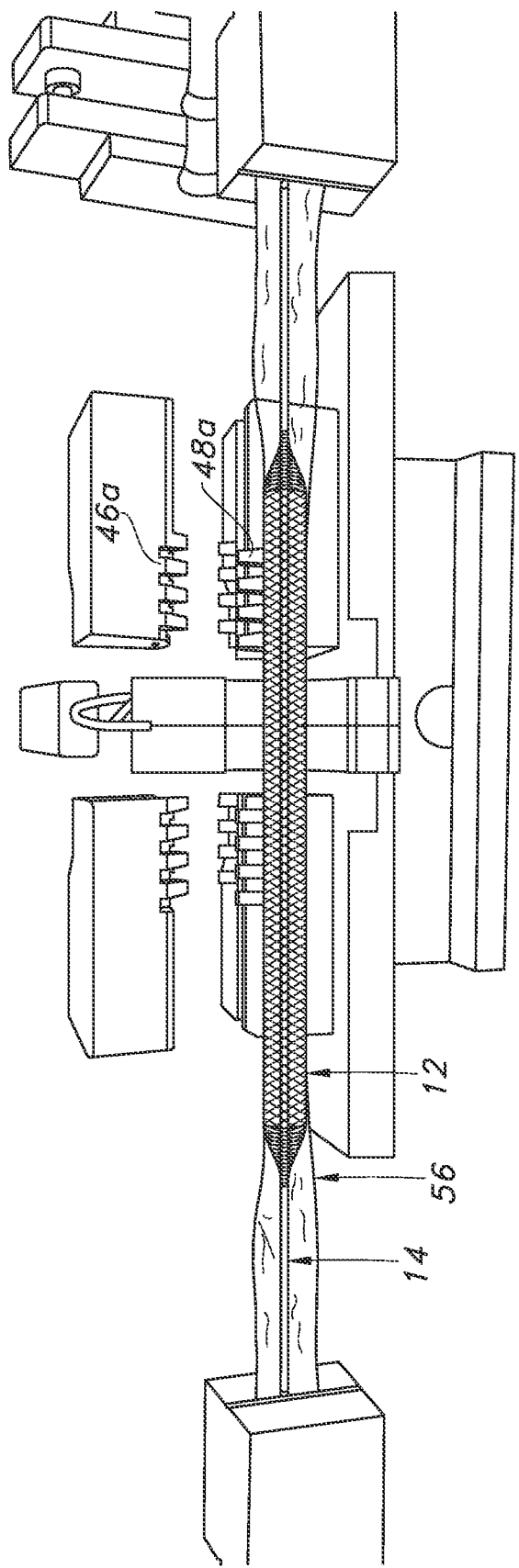
FIGS. 12-20 illustrate sequential operation of the apparatus according to one possible embodiment to apply a layer of material externally to a base balloon.

Turning first to the plan view of FIG. 1, the apparatus 10 includes a first portion adapted to receive the pre-formed base balloon 12, which as shown in FIG. 12 may include a mandrel 14 in the form of an elongated rod or tube supporting the base balloon 12 in approximately a centered position relative to the ends of the mandrel (and inbound thereof). Specifically, first and second grippers 16, 18 are provided for relative movement along a first longitudinal axis X1.

The movement of these grippers 16, 18 may be achieved by associated actuators 20, 22, which make take the form of linear actuators, which serve to independently move the grippers 16, 18 to and fro along the first axis X1.

Figure 3:
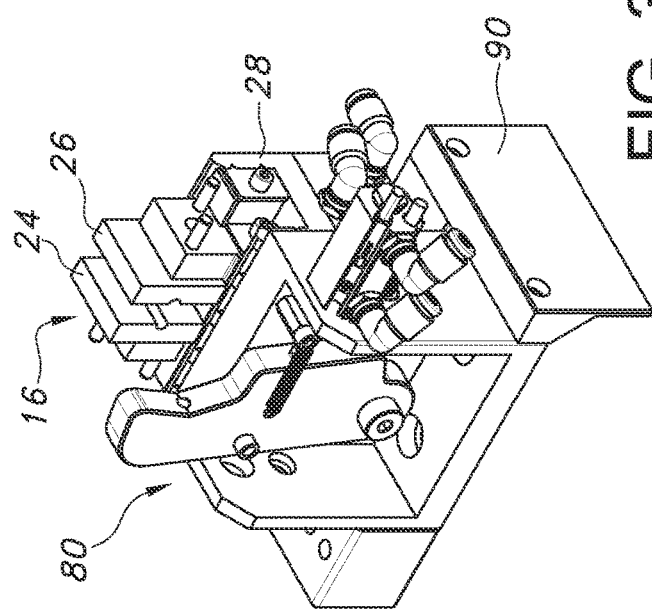
FIG. 3 is a front perspective view of a gripper and mandrel rest forming part of the apparatus.

As can be understood from FIG. 3, each gripper 16, 18 includes a pair of opposed grips shown in the form of plate-like fingers 24, 26. These fingers 24, 26 may actuate by a corresponding actuator 28 and move or clamp together to provide a gripping force on an intervening object. One or both of the fingers 24, 26 may include frictionally enhanced interior surfaces (e.g., provided with a rubberized material) to provide the desired gripping force when closed over an object.

The apparatus 10 further includes chucks 30, 32 for receiving and connecting with first and second ends of the mandrel 14. The chucks 30, 32 may be positioned outbound relative to the grippers 16, 18, as shown. One or both of the chucks 30, 32 may be associated with a rotary actuator, such as motor 34, 36, for rotating the mandrel 14 about the first axis X1.

Figure 2:
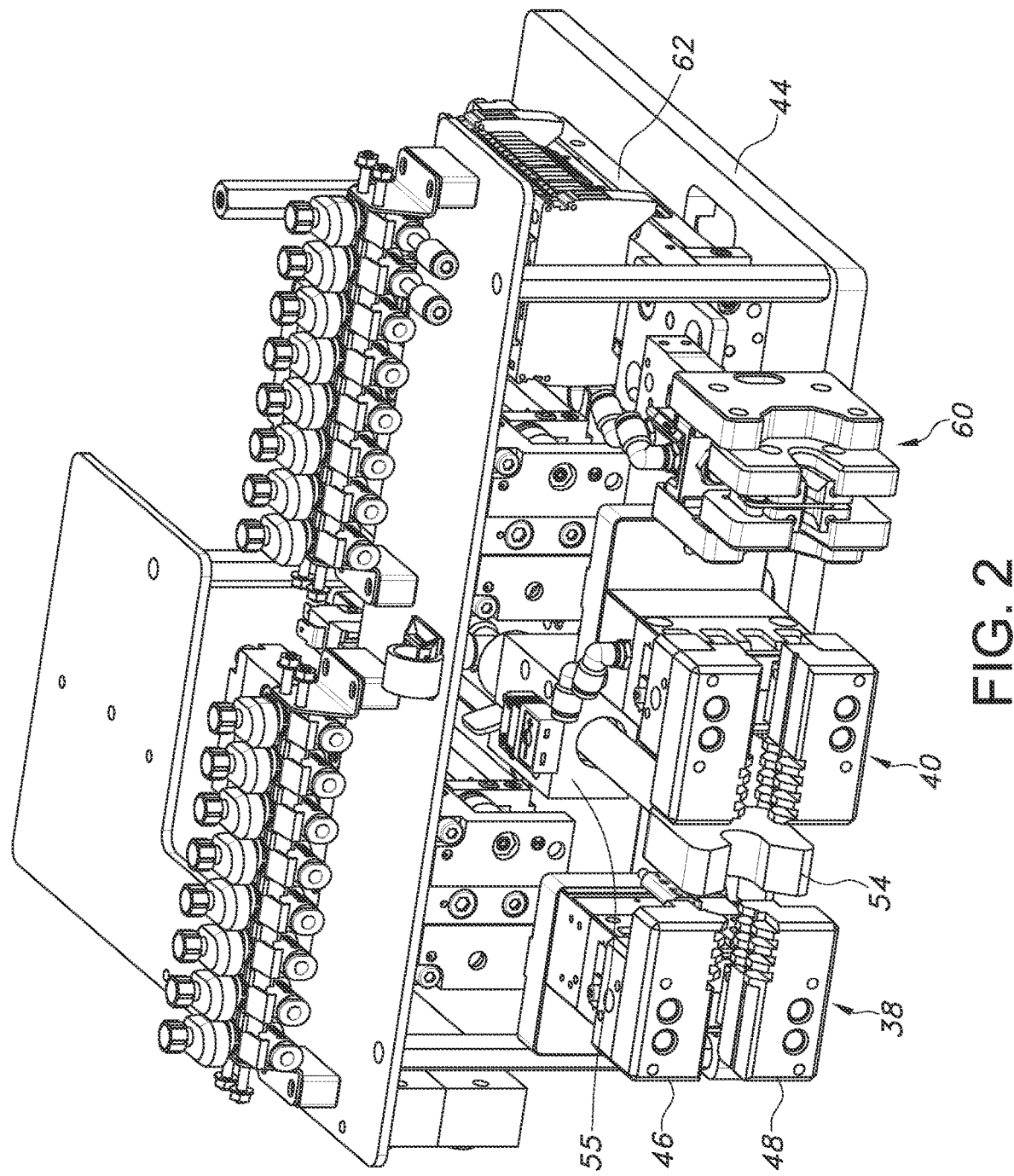
FIG. 2 is a front perspective view of a carriage forming part of the apparatus.

A second portion of the apparatus 10 is configured to interact with the base balloon 12 on the mandrel 14 when located along the first axis X1. With reference to FIGS. 1 and 2, this second portion includes one or more holders for holding the material layer to be applied against the balloon 12. In the illustrated version, a pair of holders 38, 40 are adapted both for advancing toward and away from the first axis X1 in a transverse or cross direction, and also moving along a second, parallel longitudinal axis X2.

Relative movement of the holders 38, 40 may be achieved in a variety of ways. For example, a single actuator 42, such as a linear actuator, may concurrently move both holders 38, 40 as part of a carriage 44, as shown. Alternatively, independent actuators could also be used.

The holders 38, 40 include vertically opposed retainers 46, 48 adapted to clamp down onto the base balloon 12 when positioned therebetween, such as the result of associated actuators 50, 52. The retainers 46, 48 may each include interdigitating portions 46a, 48a (see FIG. 12) to allow for variability in the degree of clamping force provided for different diameters of base balloons. The portions of the holders 38, 40 for engaging the balloon 12 may also be frictionally-enhanced, such as by including a rubberized material.

Figure 14:
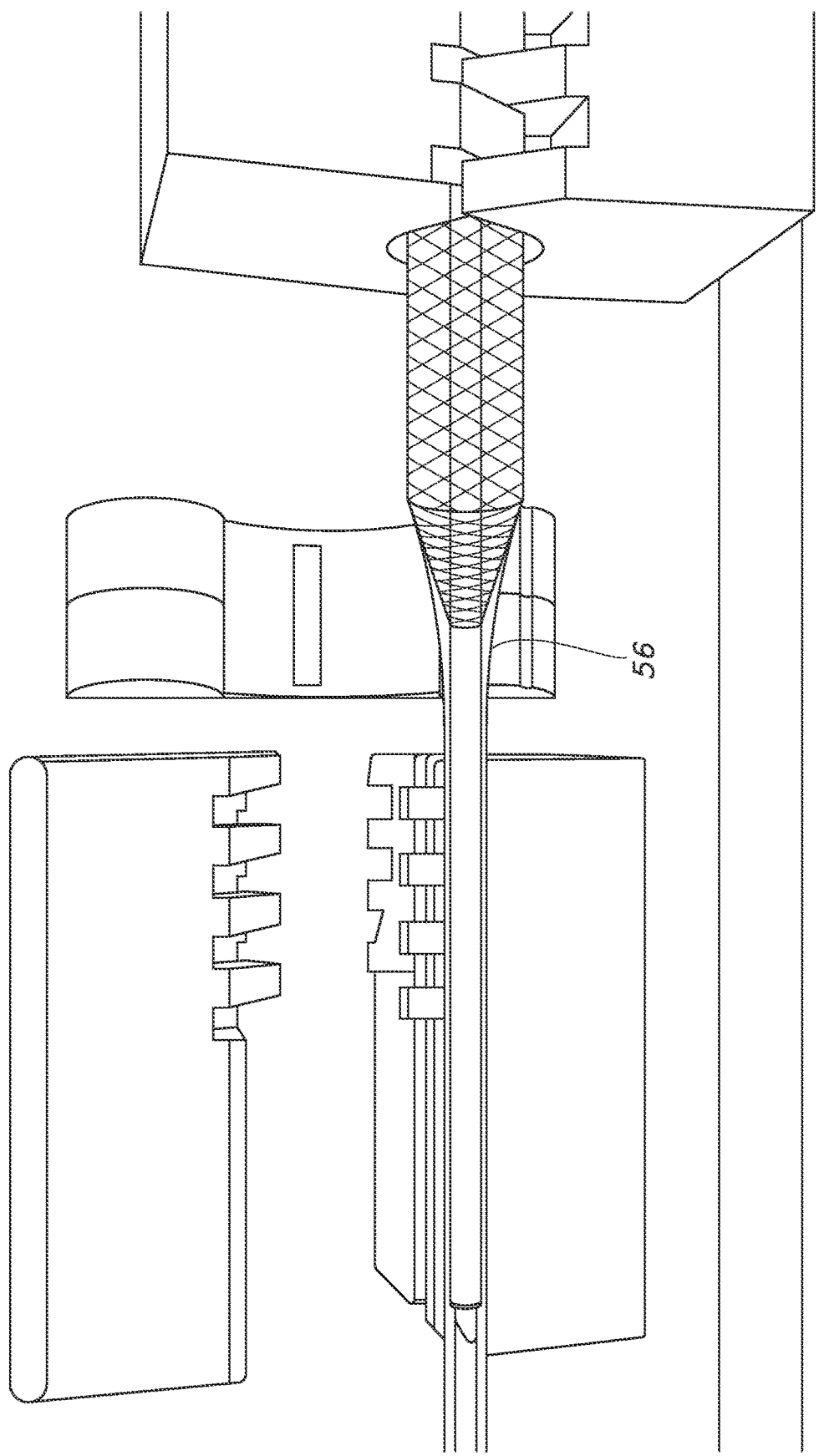

A heater 54 may also be associated with the second portion of the apparatus 10. The heater 54 is connected to an actuator 55 for moving toward and away from the first axis X1. The heater 54 may be adapted to at least partially surround the base balloon 12 in the advanced or forward position, such as by having a U-shaped or C-shaped receiver. Heated air may be delivered from the heater 54 toward the base balloon 12 via a nozzle 54a (see FIG. 14), and may move to and fro along the first axis X1, and hence the base balloon 12, as a result of the movement of the associated carriage 44 by actuator 42.

Turning to FIGS. 12-17, a description of the basic operation of the apparatus 10 in forming a balloon layer is described. As can be understood from FIG. 12, the base balloon 12 on the mandrel 14 is loaded into the apparatus 10. The material for forming the balloon layer on the base balloon 12 may also be provided concurrently, over and along the base balloon 12 and also along mandrel 14 at least to the location of the grippers 16, 18.

In the illustrated embodiment, the balloon layer initially takes the form of a tube 56 of a PET heat shrink material. This tube 56 has a diameter slightly greater than that of the base balloon 12. Other types of materials could be used in different forms (such as, for example, a sheet of film partially or fully wrapped around the balloon). The base balloon 12 as a result of the formation process may also include an adhesive along an outer surface thereof, and is shown as also including an outer fiber layer to be covered by the material of the tube 56 once secured to the base balloon 12.

Figure 13:
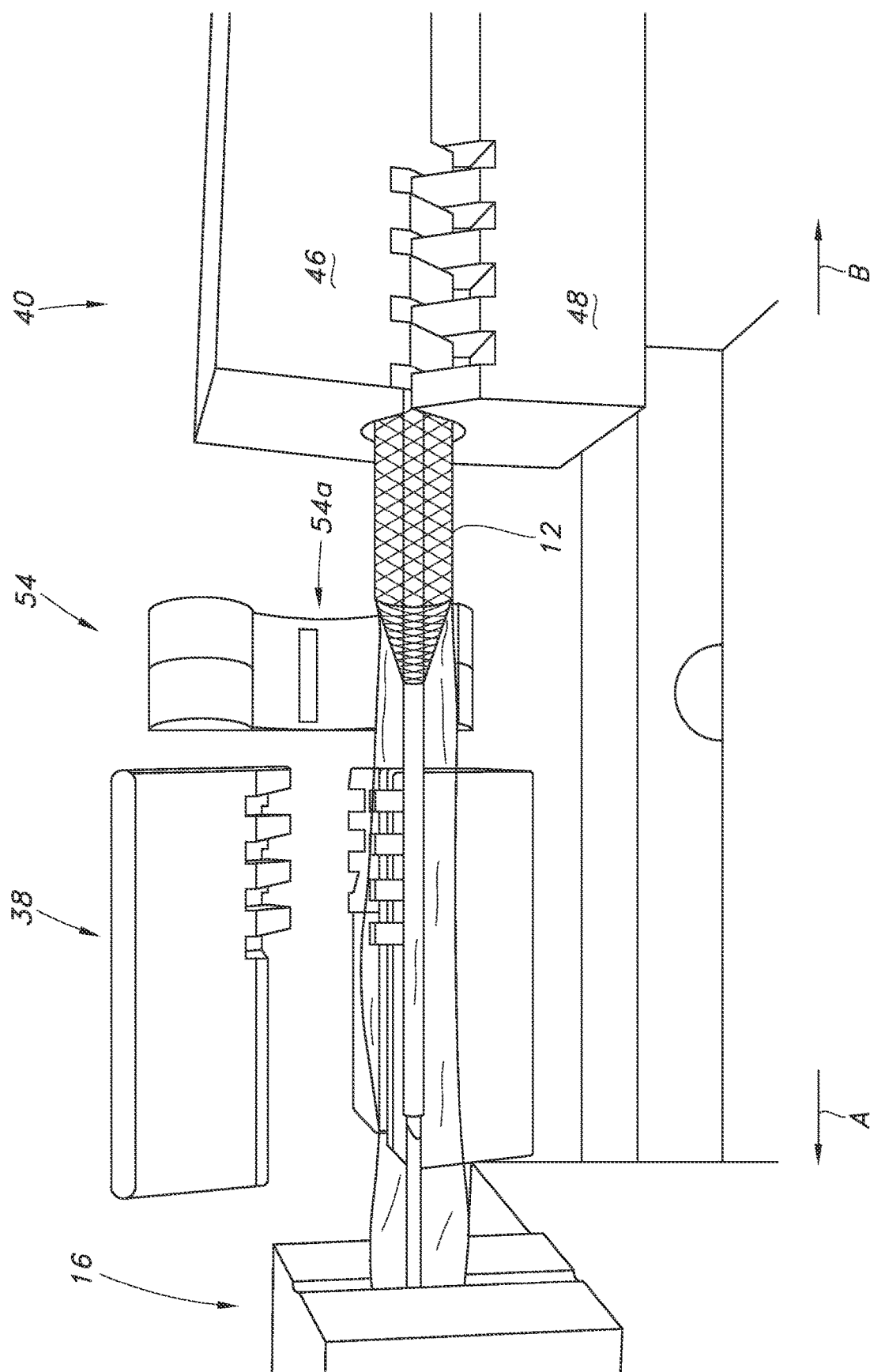

With reference to FIG. 13, one of the holders 40 is advanced (note other holder 38 retracted) such that the retainers 46, 48 overlie the cylindrical or barrel portion of the base balloon 12 including the tube 56, and are closed together to clamp down upon it. The gripper 16 adjacent to the corresponding end of the mandrel 14 is then closed such that the fingers 24, 26 grip the material of the tube 56, but not to a sufficient degree as to preclude relative movement along the corresponding portion of the mandrel 14.

The gripper 16 is then moved along the first axis X1 in a direction away (arrow A) from the base balloon 12. This causes the material of the tube 56 to stretch and "neck down" onto the corresponding portion (e.g., part of barrel, cone, and neck) of the base balloon 12 (compare tube 56 stretching from partially advanced position of gripper 16 in FIG. 13 and fully advanced position in FIG. 14). Optionally, the holder 40 may also concurrently move a relatively small amount in the opposite direction (arrow B) by way of the movement of the associated carriage 44.

Figure 15:
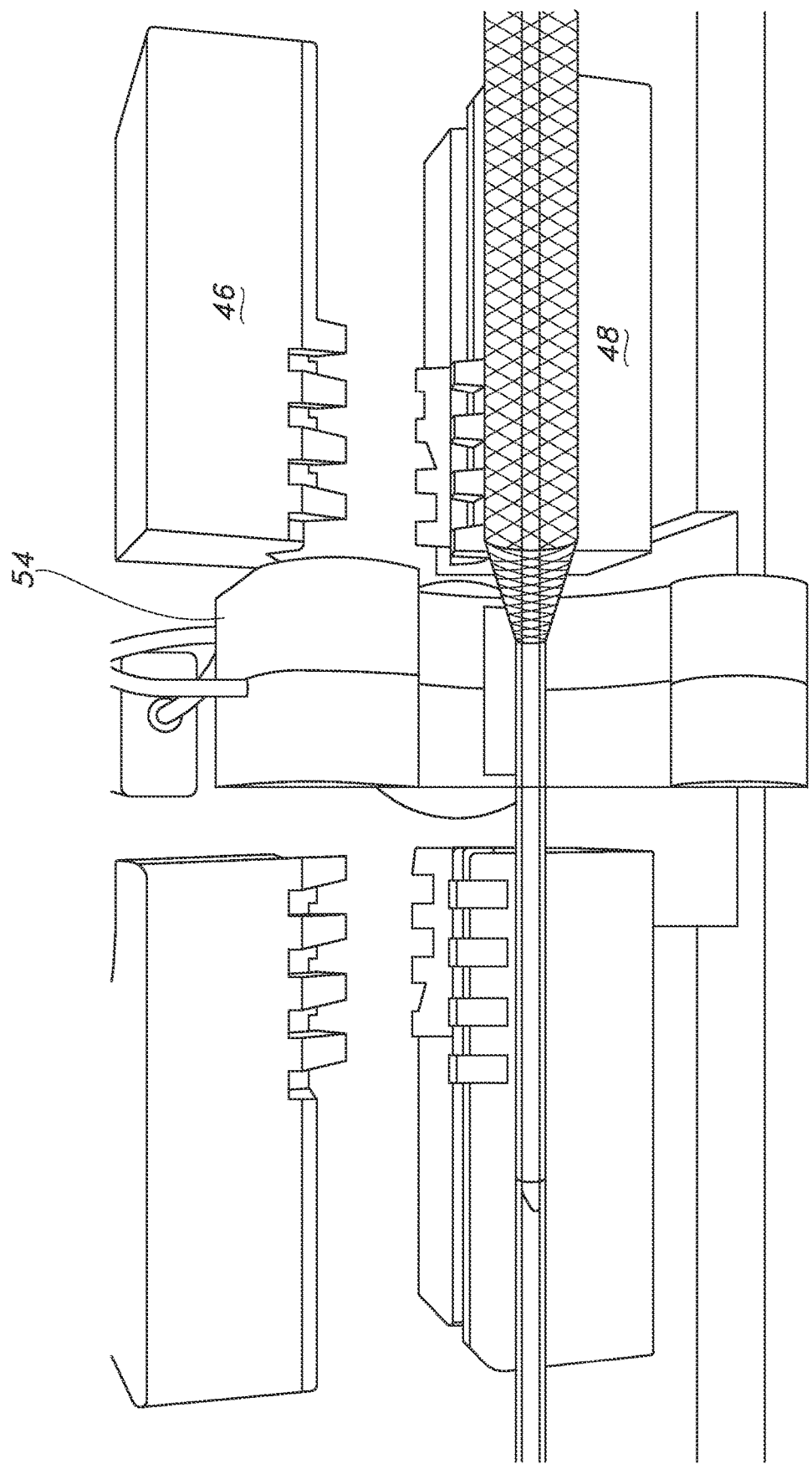

The retainers 46, 48 are then opened and withdrawn from the first axis X1, as shown in FIG. 15. The heater 54 is then moved toward the first axis X1 to adjacent the base balloon 12 including stretched layer formed by tube 56. While heat is applied, the heater 54 is then moved longitudinally along a neck, cone, and barrel of the base balloon 12, including the now-stretched portion of tube 56. In the case of a heat shrink material, this results in the desired shrinkage, thus causing the material of the tube 56 to become secured to the corresponding portion of the base balloon 12.

Figure 16:
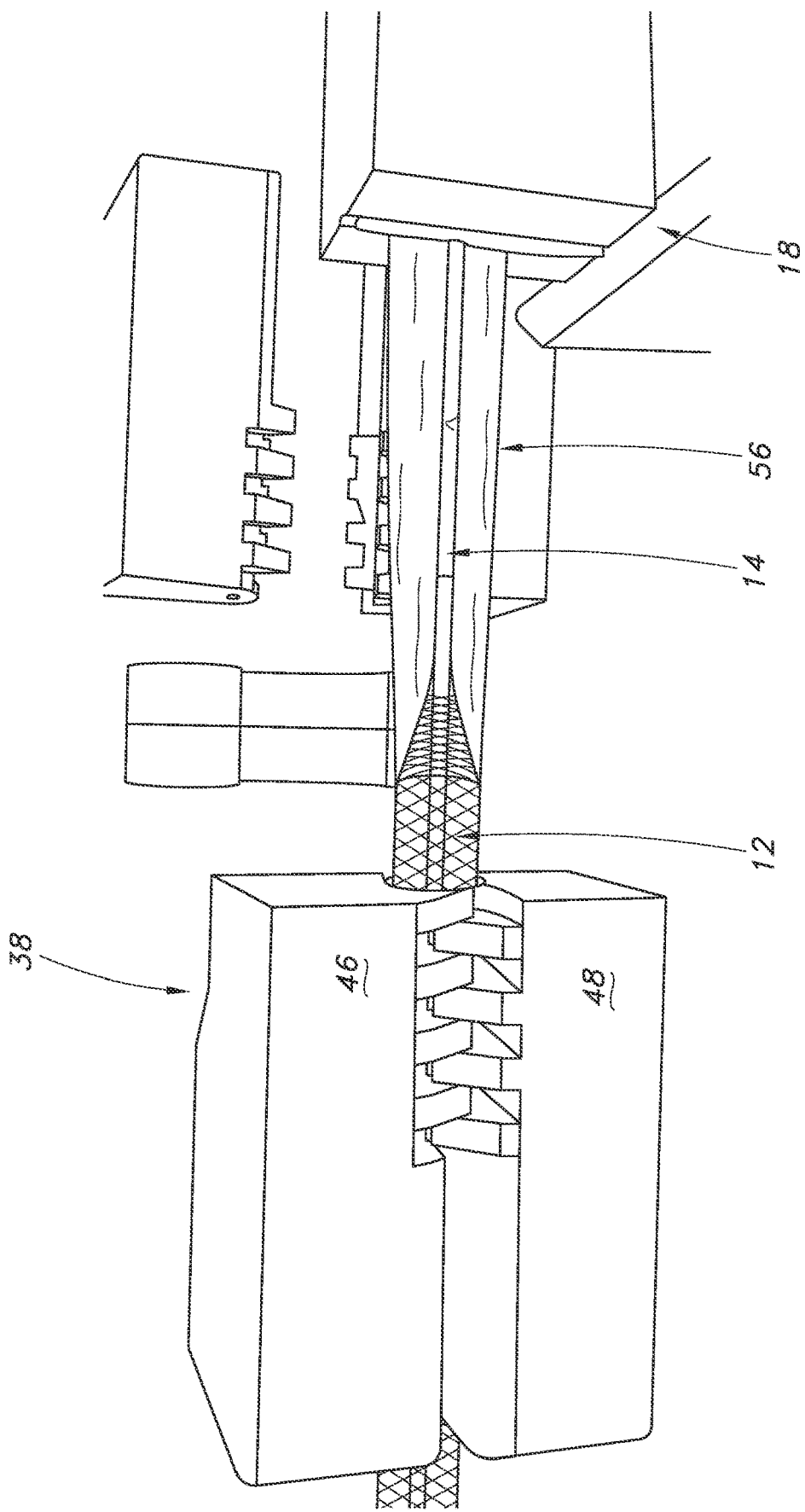
Figure 17:
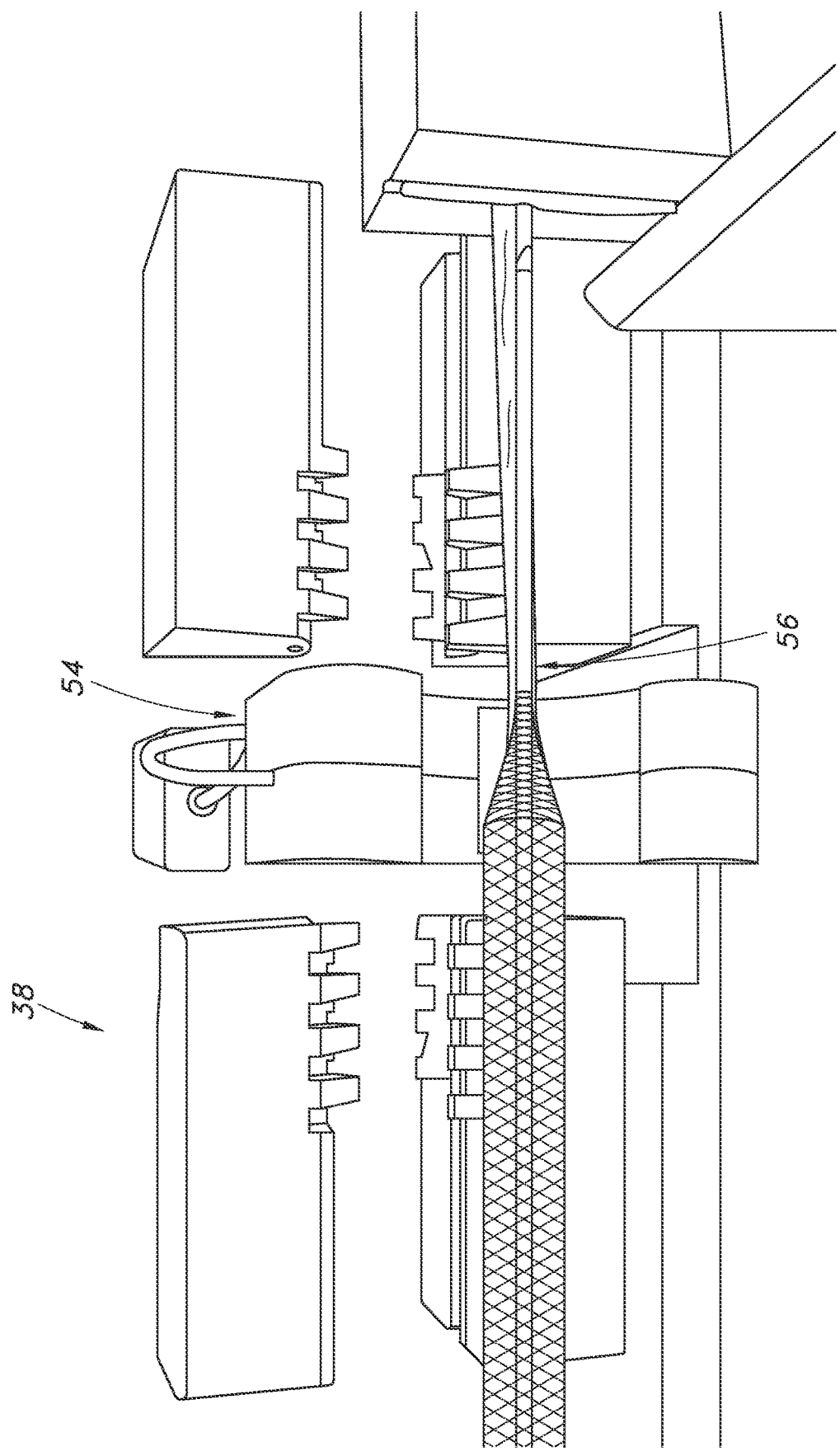
Figure 18:
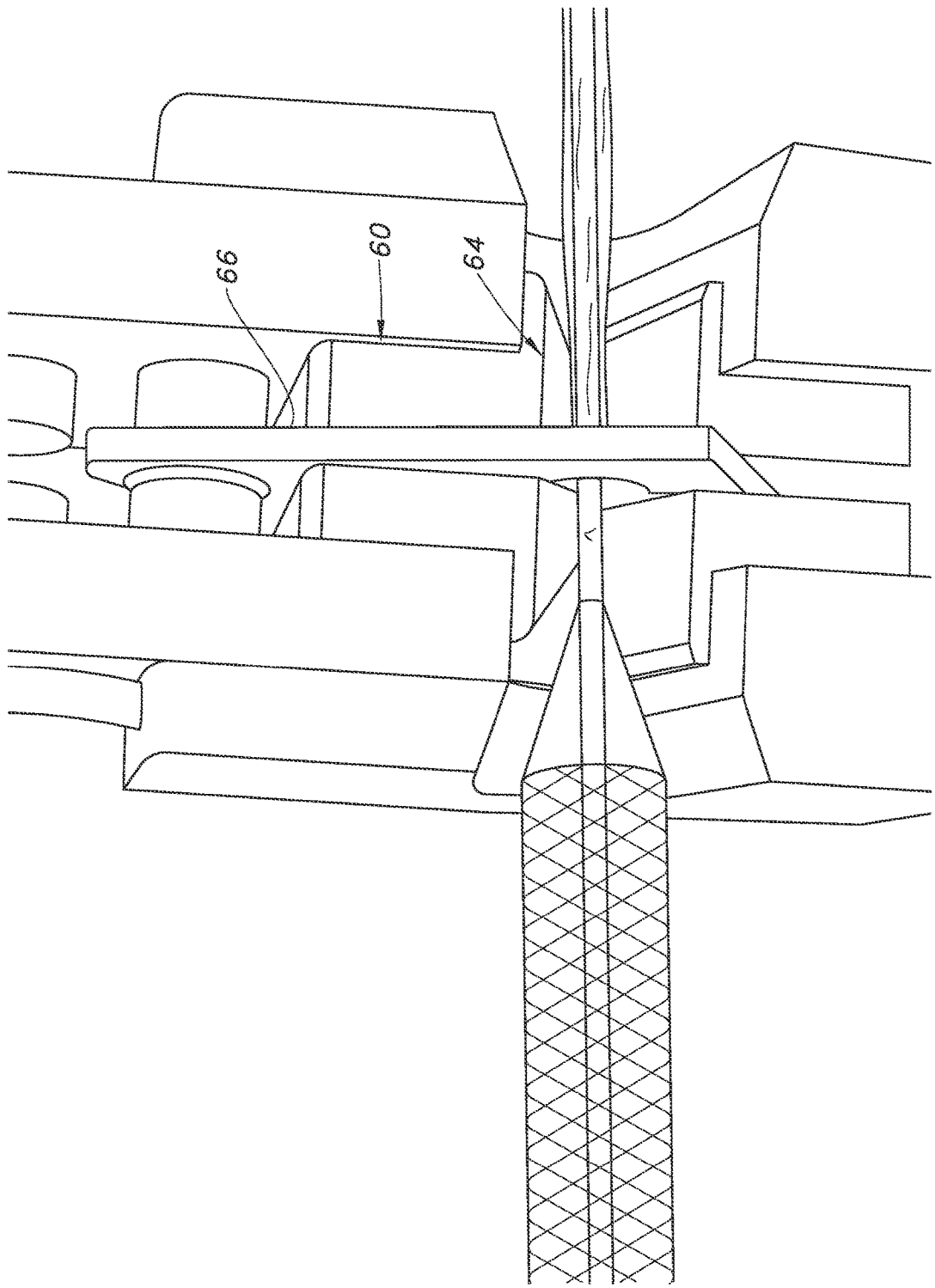

The process is then repeated for the another portion of the base balloon 12, such as the opposite end. Specifically, as shown in FIG. 16, holder 38 is moved into place and clamped, and the gripper 18 adjacent to this end of mandrel 14 is closed such that the unstretched material of the tube 56 is gripped. The gripper 18 is then moved in the opposite direction along the first axis to stretch this portion of the tube 56 (with optional movement of the holder 38 in the opposite direction). The holder 38 is then opened and withdrawn, as shown in FIG. 17, and the heater 54 advanced to apply heating to shrink the stretched portion of the tube 56 along the corresponding barrel, cone, and neck of the base balloon 12, thereby securing the material in place.

In some instances, it may be desirable to enhance the bonding between the balloon layer and the base balloon 12, such as for example at a transition between the cone of the balloon 12 and the neck. To achieve this result, a heater in the form of a heated die 60 may be provided. With reference to FIG. 2, this die 60 may be provided on the carriage 44, and may include an actuator 62 for being advanced toward the first axis X1.

Figure 5:
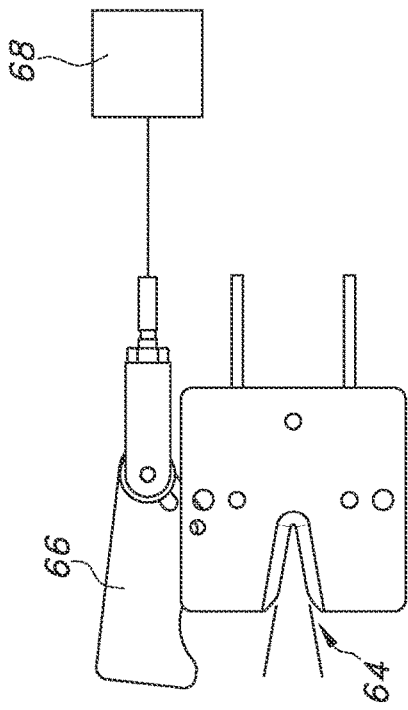
FIGS. 4 and 5 are front perspective and side views of a heated die and pusher.
Figure 4:
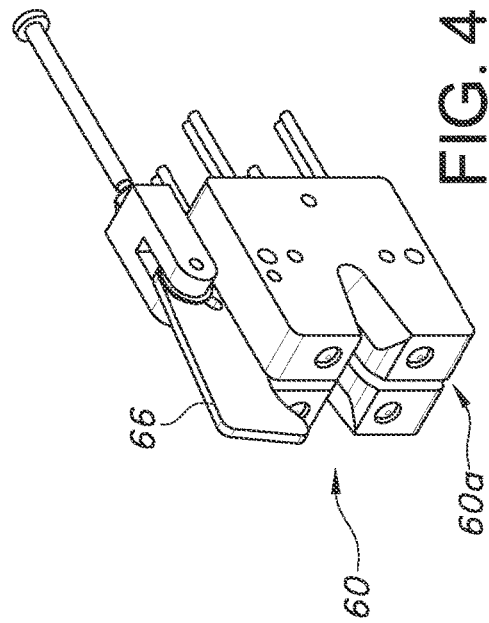
Figure 6:
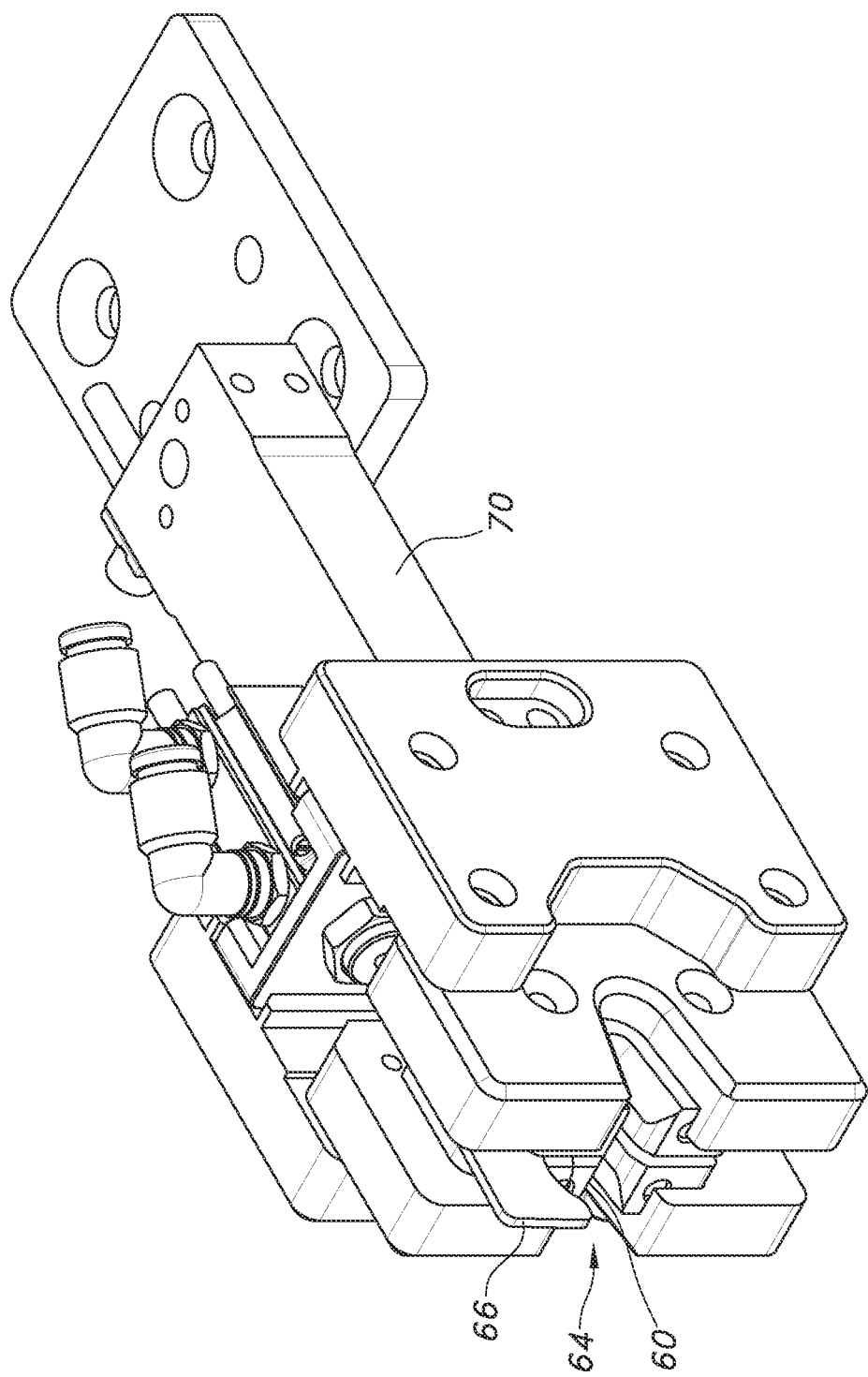
FIG. 6 is a front perspective view of the heated die and pusher associated with a sensor.

As perhaps best understood from FIGS. 4 and 5, the die 60 may include a tapered notch 64 for receiving a corresponding portion of the balloon 12 (with the added layer of tube 56 in the above example) and mandrel 14. As can perhaps be understood from FIG. 4, the notch 64 may taper in both the horizontal and vertical directions. A pusher in the form of a latch 66 associated with an actuator 68 may also be provided for entering a slot 60a in the die 60 for engaging the portion of the balloon 12 in the notch 64. This engagement urges the balloon 12 and, in particular, the outer surface of the applied balloon layer, into intimate contact with the heated die 60, thereby ensuring that the desired bonding is achieved.

To allow for the transition between the cone of the balloon 12 and the neck to be located for application of the desired bond, the die 60 may be associated with a sensor, such as a load cell 70. Thus, the die 60 is positioned over the portion of the mandrel 14 including the balloon neck and advanced toward the adjacent cone of the balloon 12, such as by movement of the associated carriage 44. When the leading end of the die 60 engages the cone during the advance, the resistance is sensed by the load cell 70 and the movement stopped, thereby properly locating the neck of the balloon 12 in the notch 64.

Figure 19:
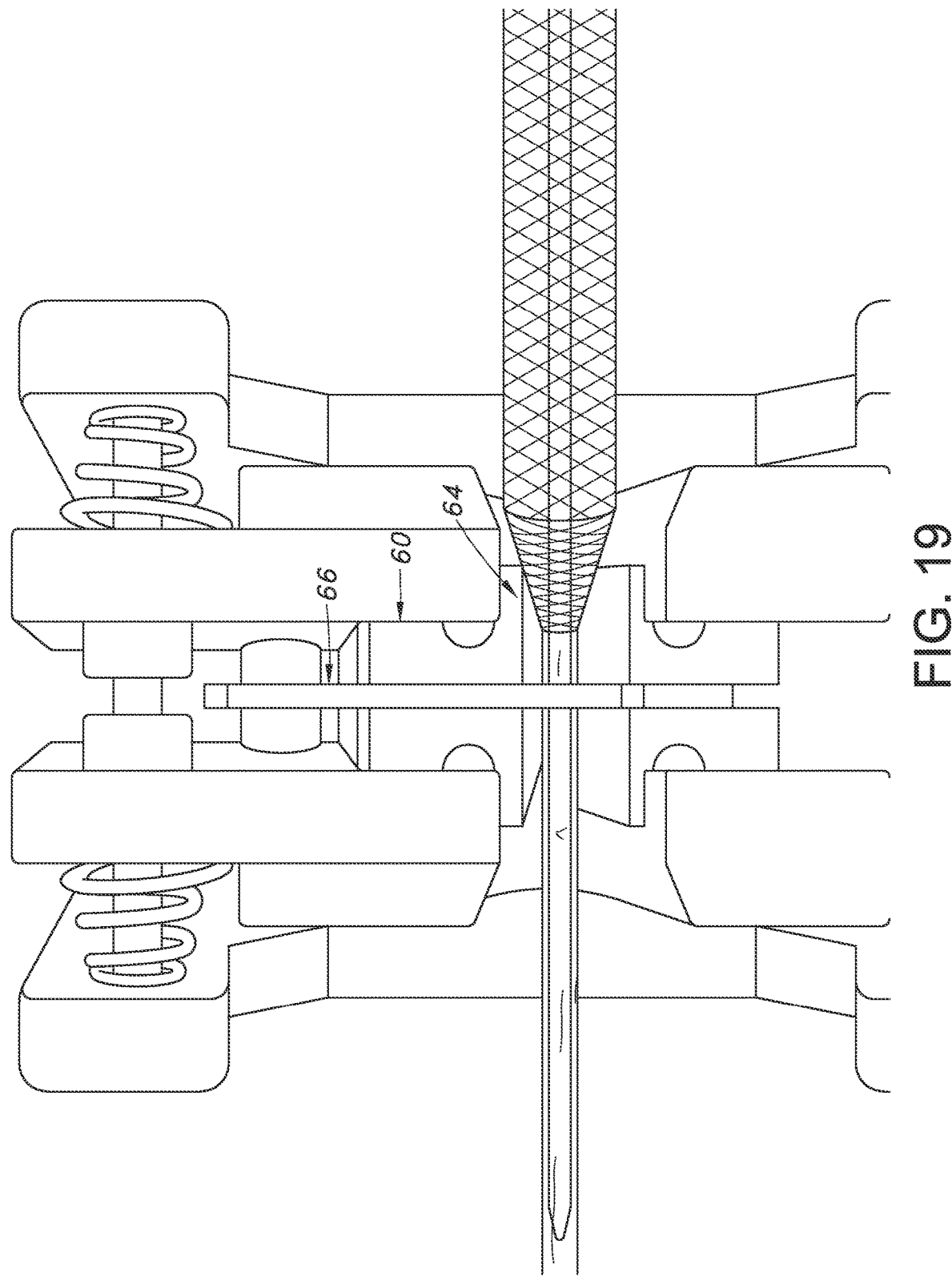

The latch 66 may then be deployed, as shown in FIGS. 7, 8, 9 (note latch positions 66 (open), 66' (partially closed), and 66" (closed)), and 18, to engage the balloon 12 with the die 60. After a suitable time to achieve a bond via the amount of heat provided, which may vary based on the material properties, the latch 66 and die 60 may be retracted. As shown in FIG. 19, the same operation may be repeated at the opposite end of the balloon 12 by simply repositioning the carriage 44 and die 60 (which can be understood may be designed to as to allow for bidirectional engagement with the balloon).

Figure 20:
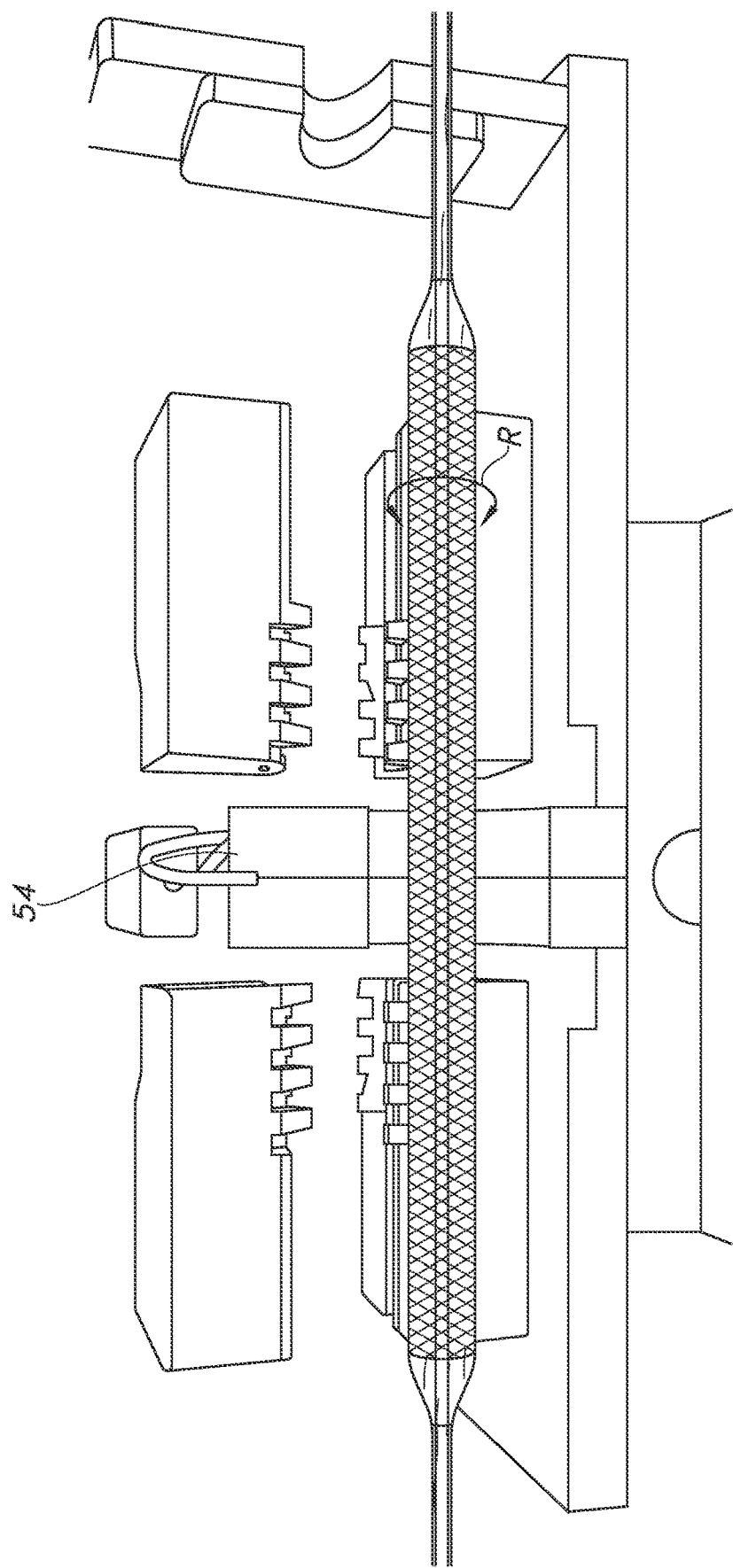

With reference to FIG. 20, it is also possible after application of the layer to apply additional heat to ensure a secure connection is established. For example, the apparatus 10 may move the heater 54 to receive the balloon 12 and apply heating while the balloon is rotated (arrow R) using the motorized chucks 30, 32 (see FIG. 1) connected to the ends of the mandrel 14. This may be done while moving the carriage 44 along the second axis X2, which thus moves the heater 54 to and fro along the rotating balloon 12.

Figure 11:
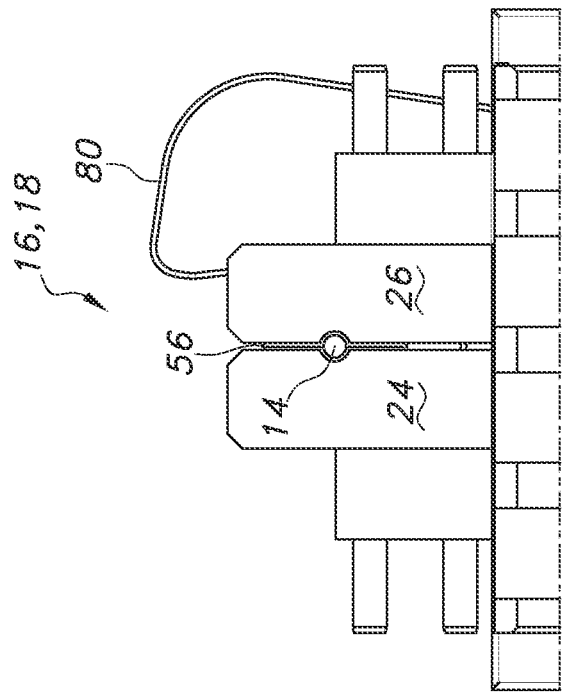
FIGS. 10 and 11 are side views of a mandrel rest and gripper in different positions.
Figure 10:
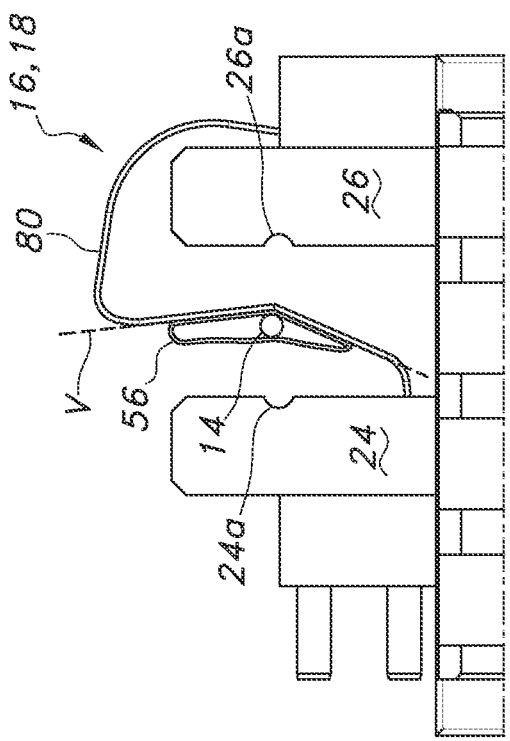

Turning back to FIG. 3, and with added reference to FIGS. 10 and 11, an optional mandrel rest 80 may also be provided adjacent to (outbound of) each of the grippers 16, 18. The rest 80 may comprise a magnetic material for coupling with the mandrel 15, which would typically be a magnetic metal. The face of the rest 80 may be V-shaped, as indicated by line V, such that when the mandrel 14 is coupled in place, the associated material of tube 56 is unbent and presents a flatter surface for being engaged by the adjacent gripper 16 or 18.

As noted above, the gripper 16 or 18 is closed over the mandrel 14 (note cutouts 24a, 26a in the face of the fingers 24, 26 for receiving the mandrel) and tube 56, as shown in FIG. 11. An actuator 82 may then retract the rest 80, breaking the magnetic coupling and allowing for free rotation or other movement of the mandrel 14 as desired. Once the process is completed, the rest 80 may be returned to a home position. The rest 80 and gripper 16 (or 18) may be mounted for combined movement on a common carriage 90, as shown in FIG. 3.

Once the layer is applied, the base balloon 12 and mandrel 14 may be removed from the apparatus for further processing, including possibly the addition of further layers. Once the balloon 12 is completed, the mandrel 14 may be removed, such as by cutting the balloon 12 therefrom at the neck portions. Once processing is complete, the balloon 12 may then be placed into service, such as by connecting it with a catheter or other medical device.

With reference back to FIG. 1, process control may be automated by a programmable controller C associated with the apparatus 10. The apparatus 10 may also include a user input, such as for example a touch screen, for specifying times, temperatures, and other parameters associated with the operation.

Although the invention has been described in conjunction with specific embodiments, many alternatives, modifications, and variations will be apparent to those skilled in the art. Accordingly, it embraces all such alternatives, modifications, and variations that fall within the appended claims' spirit and scope. For example, any or all of the parts of apparatus 10 provided on the second axis X2 could be arranged on the first axis X1 instead. Likewise, it is also possible for the grippers 16, 18 to also move the mandrel and balloon relative to the holders 38, 40. While automation of the application of the balloon layer to the base balloon is desirable, other aspects, such as the application of heat, could be performed manually instead of being automated. It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment may also be illustratively described and presented in the context or format of a plurality of separate embodiments.

All publications, patents and patent applications mentioned in this specification are herein incorporated in their entirety by reference into the specification, to the same extent as if each individual publication, patent or patent application was specifically and individually indicated to be incorporated herein by reference. In addition, the citation or identification of any reference in this application shall not be construed as an admission that such reference is available as prior art to the present disclosure.

The invention claimed is:

1. An apparatus for forming a balloon layer on an expanded base balloon, comprising:
   a mandrel supporting the expanded base balloon;
   a first gripper for gripping the balloon layer;
   a first actuator for stretching the balloon layer over the expanded base balloon;
   a first holder overlying the expanded base balloon for holding a first portion of the balloon layer over the expanded base balloon; and
   wherein the first actuator is configured to move the first gripper in a first direction to stretch the balloon layer over the expanded base balloon.

2. The apparatus of claim 1, further including a second actuator for moving the first holder in a second direction opposite the first direction.

3. The apparatus of claim 1, wherein the first gripper is adapted for gripping a second portion of the balloon layer adjacent a first end of the mandrel, and further including a second gripper for gripping a third portion of the balloon layer adjacent a second end of the mandrel.

4. The apparatus of claim 3, further including a second holder for holding a fourth portion of the balloon layer stationary while the first gripper is stretching the balloon layer.

5. The apparatus of claim 4, further including a third holder for holding a fifth portion of the balloon layer stationary while the second gripper is stretching the balloon layer.

6. The apparatus of claim 1, further including a heater for heating the balloon layer.

7. The apparatus of claim 6, further including a carriage for moving the heater along the expanded base balloon over the balloon layer.

8. The apparatus of claim 7, further including a rotary actuator for rotating the mandrel relative to the heater.

9. The apparatus of claim 6, wherein the heater comprises a heated die including a tapered notch configured for receiving and heating a portion of the balloon layer adjacent a transition from a cone of the base balloon to a neck of the expanded base balloon.

10. The apparatus of claim 9, further including an actuator for locating the heated die relative to the transition, and a pusher for urging the balloon layer at the transition into contact with the heated die.

11. The apparatus of claim 1, further including a mandrel rest configured to magnetically couple with the mandrel.

12. The apparatus of claim 11, wherein the mandrel rest includes a V-shaped face.

13. An apparatus for forming a medical balloon, comprising:
    a mandrel;
    an expanded base balloon supported by the mandrel;
    a balloon layer comprising a tubular film surrounding the expanded base balloon;
    a first gripper for gripping a first portion of the balloon layer adjacent a first end portion of the expanded base balloon; and
    a second gripper for gripping a second portion of the balloon layer adjacent a second end portion of the expanded base balloon; and
    a first actuator configured to move the first gripper in a first direction to stretch the balloon layer over the expanded base balloon or a second actuator configured to move the second gripper in a second direction to stretch the balloon layer over the expanded base balloon.

14. The apparatus of claim 13, further including at least one holder for holding a third portion of the balloon layer, and further including a first actuator configured to move the first gripper in a first direction to stretch the balloon layer over the expanded base balloon, and a second actuator configured to move the second gripper in a second direction to stretch the balloon layer over the expanded base balloon.

15. The apparatus of claim 13, further including a heated die for contacting an outer surface of the balloon layer.

16. An apparatus for forming a balloon layer on an expanded base balloon, comprising:
    a mandrel supporting the expanded base balloon;
    at least one gripper for gripping the balloon layer;
    an actuator for stretching the balloon layer over the expanded base balloon;
    a heater for heating the balloon layer, wherein the heater comprises a heated die including a tapered notch configured for receiving and heating a portion of the balloon layer adjacent a transition from a cone of the expanded base balloon to a neck of the expanded base balloon.

17. The apparatus of claim 16, further including an actuator for locating the heated die relative to the transition, and a pusher for urging the balloon layer at the transition into contact with the heated die.

18. The apparatus of claim 16, further including a carriage for moving the heater along the expanded base balloon over the balloon layer.

19. The apparatus of claim 16, further including a rotary actuator for rotating the mandrel relative to the heater.

20. An apparatus for forming a balloon layer on an expanded base balloon, comprising:
- a mandrel supporting the expanded base balloon;
- at least one gripper for gripping the balloon layer;
- an actuator for stretching the balloon layer over the expanded base balloon; and
- a mandrel rest configured to magnetically couple with the mandrel.

21. The apparatus of claim 20, wherein the mandrel rest includes a V-shaped face.

22. An apparatus for forming a balloon layer, comprising:
- an expanded base balloon supported by a mandrel;
- a first gripper for gripping a first portion of the balloon layer adjacent a first end portion of the expanded base balloon;
- a second gripper for gripping a second portion of the balloon layer adjacent a second end portion of the expanded base balloon; and
- a heated die for contacting an outer surface of the balloon layer.

* * * * *